United States Patent [19]
Duncan et al.

[11] Patent Number: 5,485,084
[45] Date of Patent: Jan. 16, 1996

[54] APPARATUS AND METHOD FOR DETECTING STRUCTURAL CRACKS USING A MOVABLE DETECTOR

[75] Inventors: Michael J. Duncan, Kent; Barry A. Fetzer; Glenn A. Geithman, both of Renton; Arthur P. Ricker, Seattle; Clyde T. Uyehara, Renton, all of Wash.

[73] Assignee: The Boeing Company, Seattle, Wash.

[21] Appl. No.: 58,183

[22] Filed: May 10, 1993

[51] Int. Cl.⁶ .......................... G01N 27/62; G01N 27/72; G01R 33/12
[52] U.S. Cl. .......................... 324/225; 324/323; 324/242
[58] Field of Search .................................. 324/225, 233, 324/242, 243, 226, 227, 262

[56] References Cited

U.S. PATENT DOCUMENTS 4,864,235  9/1989  Törnblom ................................. 324/225
5,047,719  9/1991  Johnson et al. .......................... 324/242

*Primary Examiner*—Walter E. Snow
*Attorney, Agent, or Firm*—Conrad O. Gardner; B. A. Donahue

[57] ABSTRACT

A device for detecting hidden cracks in a structure includes a hand-held probe which is moved over the surface of the structure. The probe is connected to a computer terminal which also has connected thereto a monitor and a keyboard. Changes in the eddy currents in the underlying structure generates impedance changes in the coils of the probe. The resulting voltage values produce an image of the underlying structure and any cracks therein on the computer monitor. The system utilizes a number of procedures to compensate for liftoff problems, imbalance between coil channels, and differences in impedance reference values.

7 Claims, 14 Drawing Sheets

APPARATUS AND METHOD FOR DETECTING STRUCTURAL CRACKS USING A MOVABLE DETECTOR

TECHNICAL FIELD

The present invention relates to apparatus and methods for electronically detecting hidden cracks in conductive structures.

BACKGROUND OF THE INVENTION

Early detection and correction of hidden cracks in structures such as aircraft components is important. Fatigue cracking can occur in fuselage lap joints which run longitudinally along the length of the airplane where upper skin panels overlap their adjacent lower skin panels. These panels are bonded together with adhesive and secured with multiple rows of rivets.

As a result of many pressurizations and depressurizations of the airplane, fatigue cracks can develop under and adjacent to the rivet locations. These cracks may develop below the surface of the airplane skin and thus may not be detectable by the naked eye. Furthermore, a typical commercial airliner has several thousand rivet locations. Therefore it is desirable to provide means for quickly and accurately detecting the presence of these fatigue cracks.

Historically, testing devices employing eddy currents have been used to detect structural flaws. Typically these induced eddy currents, which are present in the aluminum structure, produce magnetic fields which oppose the magnetic fields produced by the coils in the testing device. If there is a crack in the test structure, the eddy currents are disrupted causing the impedance in the tester coils to rise. This impedance change is detected by the tester and used to provide a visual indication of the crack.

A number of conventional devices for detecting hidden cracks have been disclosed. For example, in U.S. Pat. No. 4,134,067 by Woodbury, and assigned to the assignee of the present invention, discloses an eddy current device for detecting cracks in metal surfaces such as the walls of rivet holes in aircraft pans by using a rotary detection probe. Furthermore, U.S. Pat. No. 4,207,520 by Flora et al discloses a computer based device for detecting cracks under installed fasteners as a function of a phase difference between two signals.

SUMMARY OF THE INVENTION

The present invention pertains to apparatus for detecting a crack in a workpiece, such as a metallic structure. The apparatus includes means, which are movable with respect to the workpiece, for detecting a change in an eddy current in the workpiece due to the presence of the crack when the detecting means is moved near the crack. In addition, there are means for generating a signal which is a function of the change in the eddy current due to the presence of the crack. Furthermore, there are means for generating a visual display of the crack as a function of the generated signal.

BRIEF DESCRIPTION OF THE DRAWINGS

Other features and advantages of the present invention will be described in the following Detailed Description, in which.

DETAILED DESCRIPTION

The present invention broadly relates to a device for detecting irregularities in conductive materials. In an exemplary embodiment, the present invention relates to a device for detecting cracks in aircraft metallic structures.

Figure 1:
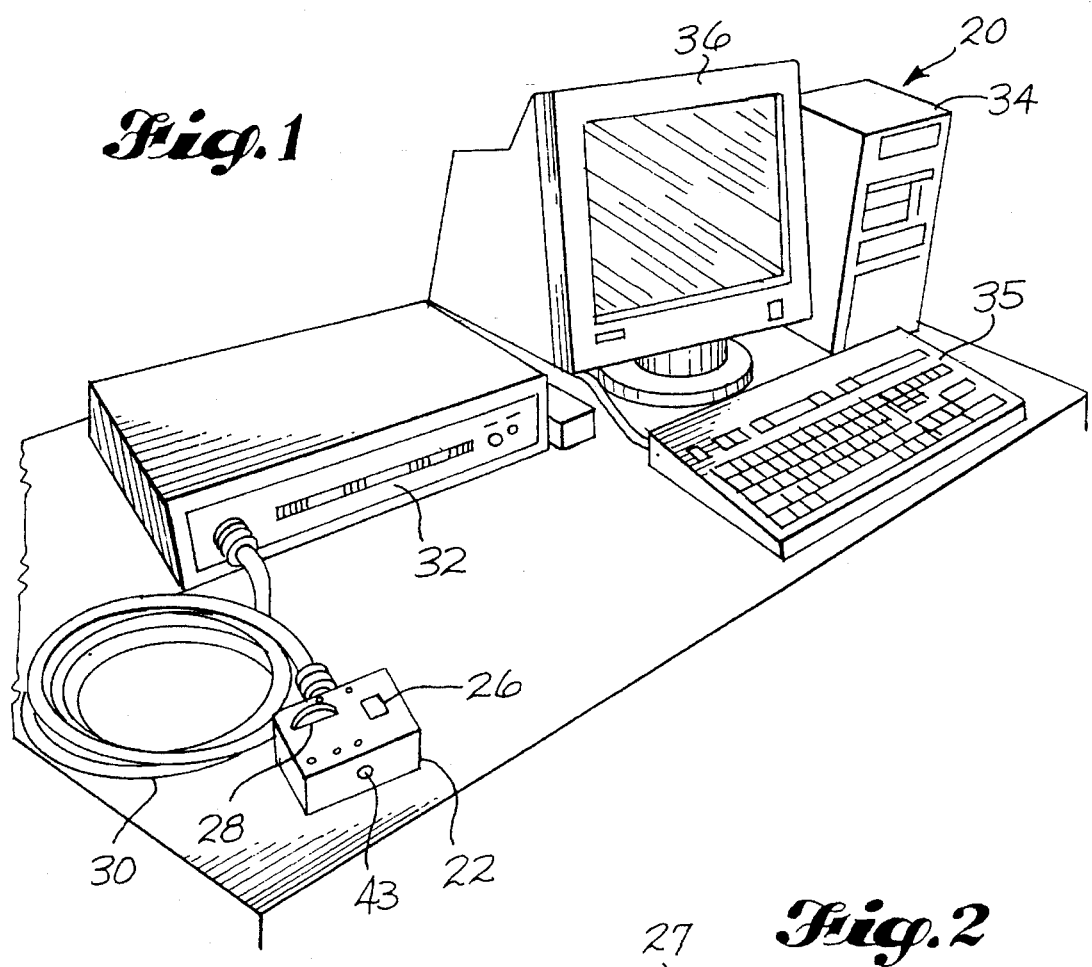
FIG. 1 is pictorial representation of the components of the present invention.
Figure 2:
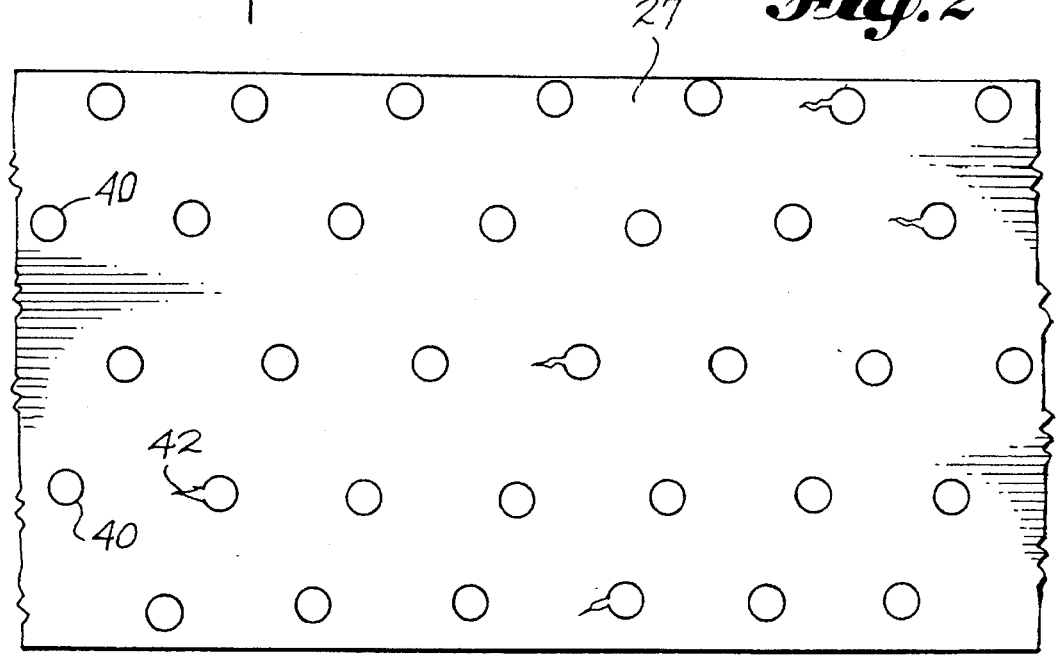
FIG. 2 is a pictorial representation of an airplane skin panel having a plurality of rivet holes with small machine cuts extending from some of the holes to simulate stress cracks.
Figure 3:
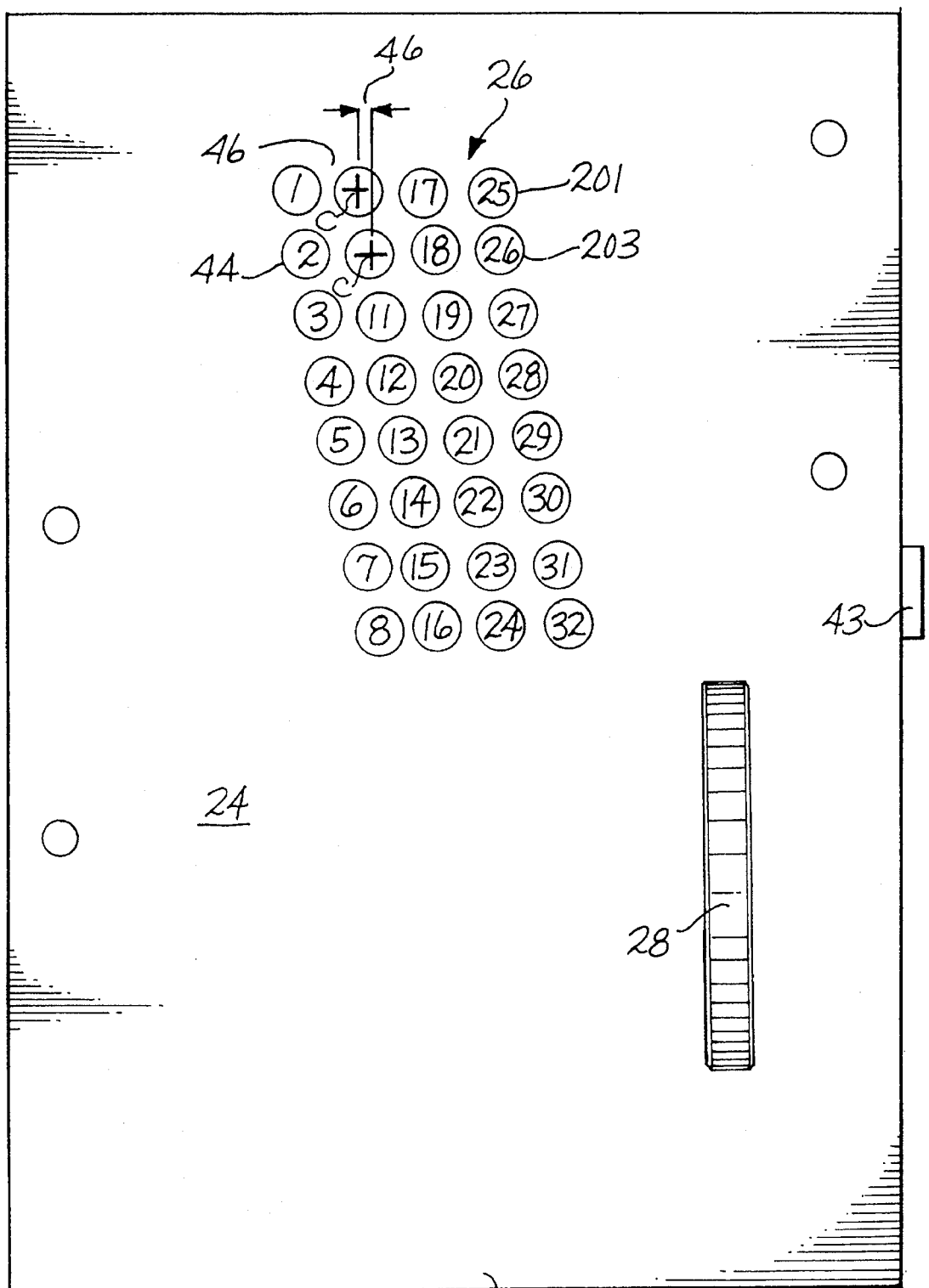
FIG. 3 is a plan view of the bottom of an eddy current array probe of the present invention.

Referring first to FIGS. 1 & 3, there is shown a detection and display system of the present invention generally indicated at 20. The system 20 includes a hand held probe 22 having a bottom surface 24 which exposes the bottom ends of a number of coils 26. In order to test a part for cracks, an operator positions the coils 26 over the area to be tested (part-under-test 27 in FIG. 2) and guides the probe 22 along the surface of the part 27 by means of a rotary wheel 28 which extends below the bottom surface 24.

In the present invention, the coils 26 are excited by high frequency energy. When the coils 26 are brought in close proximity to aluminum, eddy currents in the aluminum are generated by induction. The eddy currents produce a magnetic field which opposes changes in the coil's magnetic field which in turn has the effect of reducing the impedance of the coil. However, if there is a crack in the part-under-test, when the probe is over the crack the eddy currents are disrupted causing the impedance in the coils 26 to rise. This sudden rise of impedance is detected by the present system and used to provide a visual indication of the crack.

More specifically, electrical signals from the probe 22 (FIG. 1) are conducted via a coaxial cable 30 to a box 32 containing electronic circuitry for processing the probe signals for use by a downstream IBM clone digital personal computer 34. The computer 34 contains software instructions (to be discussed in detail) for converting the probe signals into the proper format for displaying cracks in the part-under-test on a conventional video monitor 36. Operation of the system 20 is controlled from a conventional computer keyboard 38 which is also electrically connected to the computer 34. As shown in FIG. 2, the part 27 displayed on the monitor 36 includes a number of rivet holes 40, some of which have small (simulated) fatigue cracks 42 extending in a horizontal direction from the edges of the holes. By pressing a data acquisition button 43 on the probe a menu for selecting liftoff, balance and zeroing compensation procedures (to be discussed later) is displayed on the monitor.

Referring now to FIG. 3, the ends of the coils 26 at the bottom surface 24 of the probe 22 are shown in more detail. Specifically, the coils 26 are cylindrical ferrite rods wrapped with forty two gauge magnet wire to produce an inductance of about one hundred microhenries. Each coil 26 has a diameter of about 110 mils and generates a magnetic field having an effective radius of about thirty mils. In order to prevent gaps in the coverage of the magnetic field, it is desirable to position the coils 26 so that their centers are no more than about twenty five mils apart. To accomplish this, each succeding row of coils is "staggered" twenty five mils to the right of the above row. That is, for example, the center C of each coil in row #2 (which is identified by the number 203) is twenty five mils to the right of the center of the coil directly above it and this distance is identified by the number 46 in FIG. 3.

In an exemplary embodiment, the total number of coils 26 is thirty two, which is a sufficient number to provide satisfactory resolution for detection and display of structural skin cracks, but not so many that the device becomes too complicated. This results in the coil array having a width dimension of about one inch which is large enough to scan an entire rivet head. Furthermore, a coil frequency of about one hundred KHz is utilized to allow for detection of cracks about fifteen thousandths of an inch below the part surface.

Figure 4:
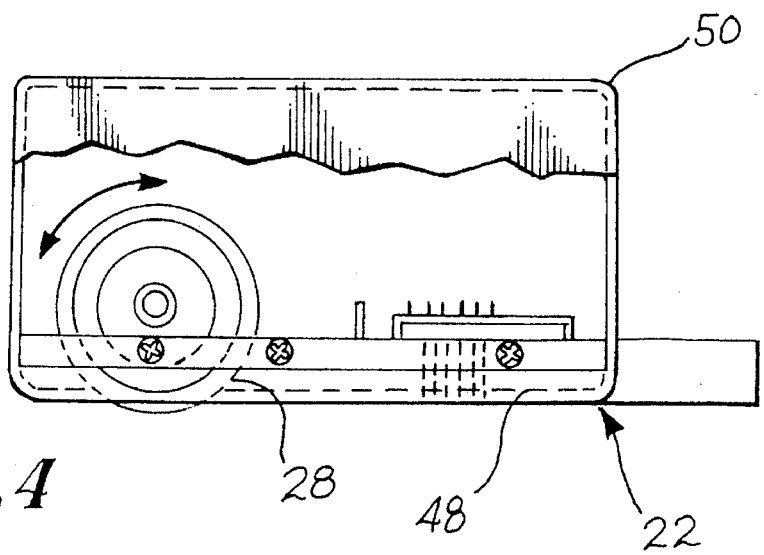
FIG. 4 is a top view of the inside of the eddy current array probe.
Figure 5:
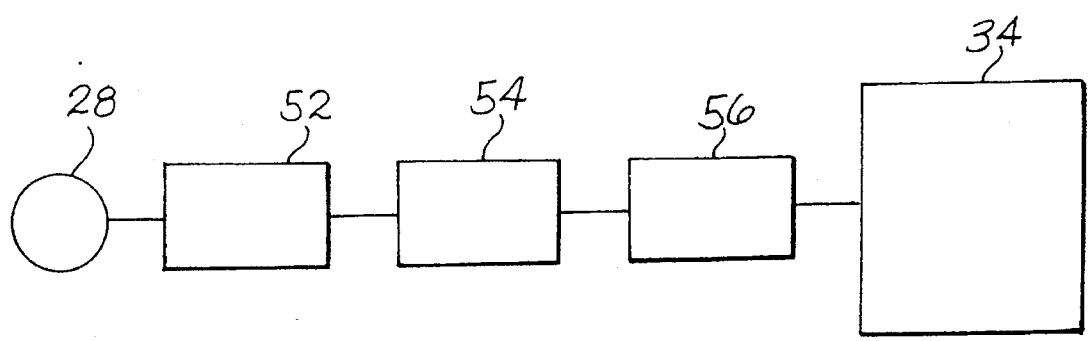
FIG. 5 is a block diagram of the probe electronic components for providing probe location information.

As shown more clearly in FIG. 4, the probe 22 includes a nylon base plate 48 and an aluminum cover 50. The rotary wheel 28 (FIG. 5) is connected to a conventional incremental optical shaft encoder 52 to provide position information. During rotation of the wheel 28, a light beam in the encoder is interrupted by a rotating code wheel connected to the rotary wheel 28 thereby generating an electrical pulse for each increment of shaft rotation. The shaft encoder output is buffered in a conventional manner (such as described in Hewlitt Packard Application Note 1011 "Design and Operational Considerations for the HEDS-5000 and HEDS-6000 Incremental Shaft Encoders"). The shaft encoder operates so that 1024 interrupt pulses are generated per wheel revolution. The wheel 28 is sized so that three hundred interrupt pulses are generated per inch of wheel travel. This output is then sent through a conventional divide-by-seven circuit 54 so that a pulse is generated each 12.5 mils of wheel travel (eighty pulses per inch). The resulting signal is fed to a conventional address counter 56 which generates a binary output representative of wheel position. The binary output is then sent to the computer 34 where it is used to determine the real time position of the probe in a manner to be discussed later.

Figure 6:
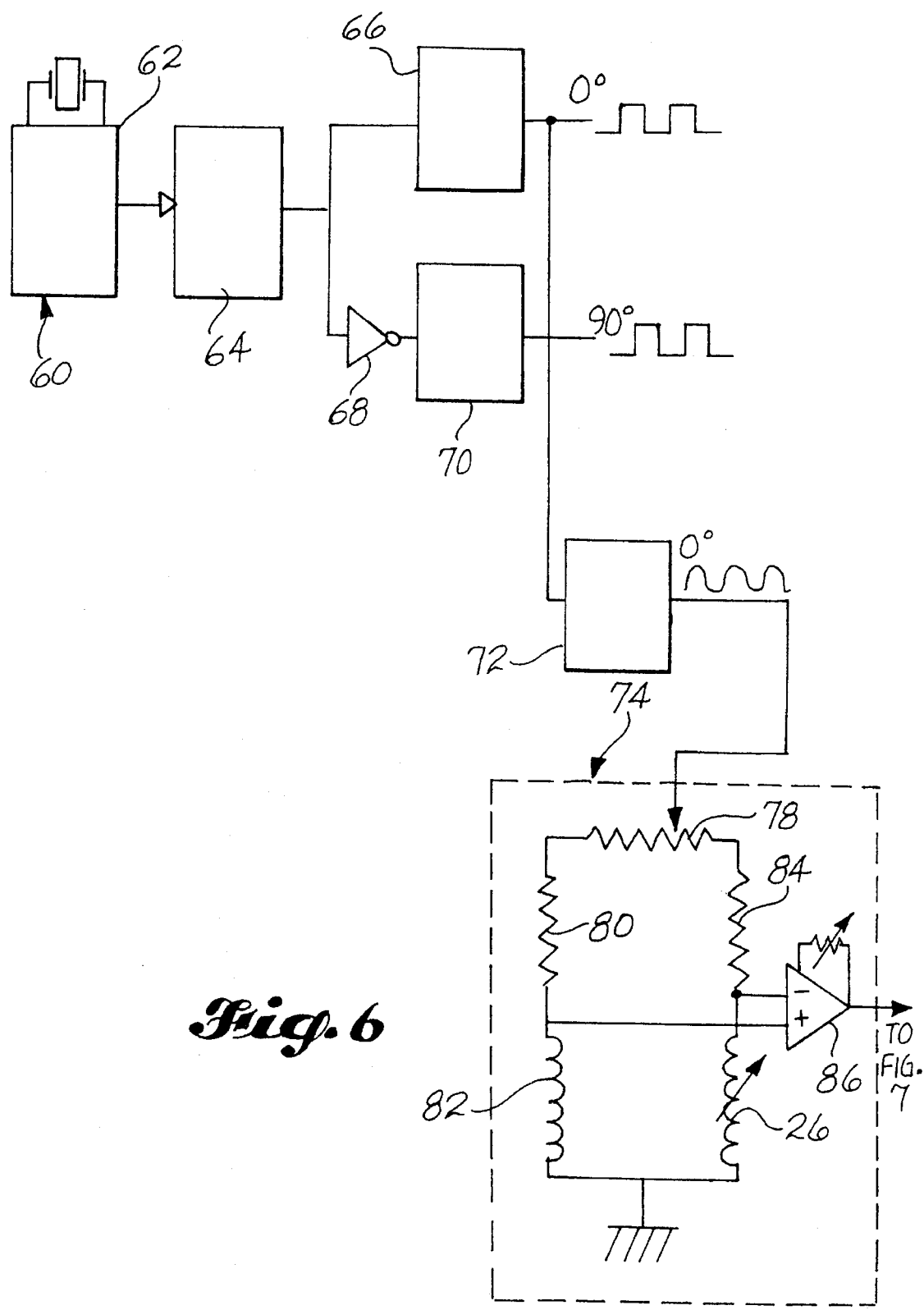
FIGS. 6 and 7 are block diagrams of the electronic components for providing probe signal generation and voltage in-phase and quadrature signals.

In the present invention, a one hundred KHz sinusoidal signal is sent to each coil 26. This signal is generated by an oscillator circuit indicated at 60 in FIG. 6. More specifically, the oscillator circuit 60 includes a four MHz crystal oscillator 62 which is reduced down to two hundred KHz by a downstream divider circuit 64. The resulting output is fed through (i) a first branch to a rising edge-triggered flip flop 66 to generate a one hundred KHz square wave having zero degrees phase shift, and through (ii) a second branch through an inverter 68 to a falling edge-triggered flip flop 70 to generate a one hundred KHz square wave having a ninety degree phase shift. These; resulting signals are used for timing purposes in a manner to be described later.

In addition to providing one of the aforementioned timing signals, the zero degree phase shifted output from the flip flop 66 is fed to a one hundred KHz high band filter 72 which converts the input to a one hundred KHz sine wave which is fed to a conventional bridge circuit indicated at 74 Briefly, this sinusoidal signal passes through the bridge and generates an electromagnetic field. If the probe passes over a crack in the part, the impedance of the detector coil is increased, thereby creating an imbalance voltage in the bridge which is equal to the difference between the voltages across a detector coil and a reference coil in the bridge.

More specifically, the sinusoidal signal from filter 72 is fed through a potentiometer 78; the potentiometer being used for balancing the bridge circuit. Connected to the left end of the potentiometer 78 is a resistor 80 which is connected in series with a reference coil 82 which in turn is connected to ground. The other end of the potentiometer 78 is connected in series to a resistor 84 which in turn is connected to the detector coil 26. Any difference (for example due to a crack in the part-under-test) between the magnetic field at reference coil 82 and at detector coil 26 appears as a voltage difference at the inputs to an amplifier 86 which has its positive input connected to the junction between resistor 80 and reference coil 82, and its negative input connected to the junction between resistor 84 and detection coil 26. It should be appreciated there is one bridge circuit 74 for each coil 26.

A feature of the present invention is the elimination of any unwanted signals due to "liftoff". More specifically, liftoff is caused by the tendency of the probe 22 to move in a vertical direction as it is moved across the part-under-test due to undulations in the surface of the part. As a result, this liftoff can result in erroneous and unwanted signals being generated by the probe. To eliminate any signals due to liftoff, the output from amplifier 86 is fed to two parallel conventional synchronous detectors 90, 92 shown in FIG. 7. In the present invention, the sync detector at 90 is controlled by the zero degree timing signal from flip flop 66 (FIG. 6) and the sync detector 92 is controlled by the ninety degree timing signal from flip flop 70. In this manner, the output from sync detector 90 is an in-phase one hundred KHz signal component, and the output from sync detector 92 is a one hundred KHz signal component which has a ninety degree phase shift. In order to eliminate the high frequency components from each of these signals, they are filtered by respective downstream low pass filters 94, 96 (having one KHz rolloffs). The resulting output signals are sent to a conventional multiplexer 100 which receives thirty two in-phase signals from sync detector 92 and thirty two quadrature signals from the sync detector 94. These signals then are fed to a conventional one hundred KHz analog-to-digital converter 102 inside computer 34.

An advantage of the present invention is the ability to perform liftoff compensation in real time. That is, many conventional measurement systems require a time consuming liftoff compensation procedure prior to being used. In the present invention, liftoff is performed rapidly and automatically. In this manner, liftoff compensation can be accomplished not only prior to a crack detection procedure, but also during the crack detection procedure so that the liftoff compensation values can be updated to reflect changes in the part-under-test.

As mentioned previously, the present invention measures the change in impedance in each coil caused by the coil being moved across the crack. This impedance change results in a change in voltage which is a complex variable having a real component and an imaginary component. In a graphical plot of voltage, the real component (which represents energy loss) always appears on the x axis and the imaginary component (which represents stored energy) always appears on the y axis.

Figure 8:
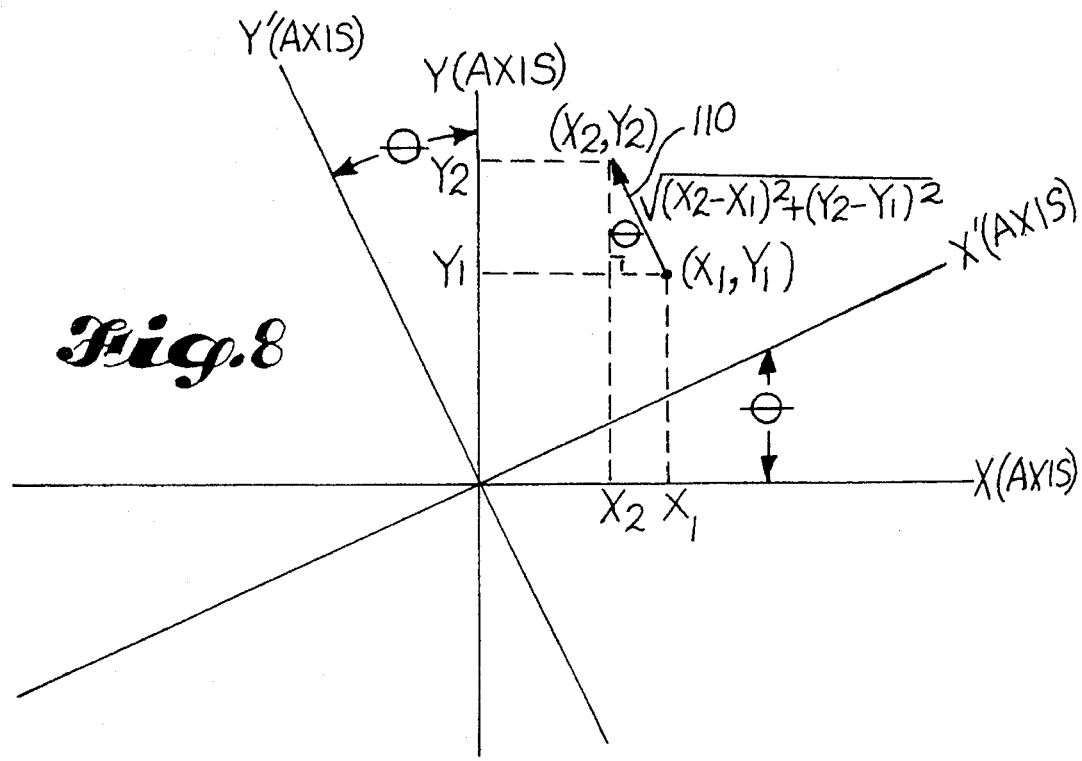
FIG. 8 is a graphical plot of two separate voltage in-phase and quadrature components for calculating liftoff constants.

For example, measurement of the impedance of a first surface $S_1$ will produce voltage components $(x_1, y_1)$ which are plotted graphically in FIG. 8. Furthermore, if the impedance of a second surface $S_2$ is measured and the surface $S_2$ has a smaller resistive component and a larger inductive reactance component, then the resulting voltage components $(x_2, y_2)$ would appear as shown in FIG. 8.

However, in the present invention it is important not to measure any component of impedance caused by vertical movement of the probe coils (liftoff). Rather, it is desirable to measure only changes in impedance caused by the presence of cracks in the part-under-test. More specifically, changes of impedance can be caused by movement of the probe coil vertically towards or away from the part-under-test. If this change in impedance due to liftoff is not compensated for, it can result in the display of false cracks or in the failure to display actual cracks which are present in the part-under-test.

Changes in impedance due to liftoff cause changes in both the real and imaginary components of impedance. Moreover, changes in impedance due to the presence of a structural crack cause changes in the real and imaginary components as well, but not in the same proportion as the changes due to liftoff. In the present invention, the coordinate system is rotated so that the undesirable vector (liftoff) is aligned with the y-axis of the coordinate system. The impedance component along the y-axis is then ignored and only those changes in impedance along the x-axis are utilized. In this manner changes in impedance due to liftoff are eliminated for small changes in liftoff.

In order to accomplish this, an initial procedure is performed whereby the impedance of two different surfaces are measured which have different impedances due only to liftoff differences. This, in turn, is done by measuring the impedance of an area directly on the pan-under-test and generating voltage components $x_1, y_1$, and then measuring the impedance of the same area of the pan-under-test which has been covered by three sheets of a polyester film such as Mylar (a registered trademark of DuPont de Nemours, E. I. & Co.) and generating voltage components $(x_2, y_2)$.

This results in a vector 110 (FIG. 8) from point $(x_1, y_1)$ to point $(x_2, y_2)$ at an angle theta relative to the original y-axis. It is desirable to eliminate the vector 110 from any future measurements since this is the voltage component due to liftoff. For small changes in liftoff, it can be assumed that vector 110 is a straight line and therefore the effects of liftoff can be eliminated to a first order approximation. This is accomplished by rotating the coordinate system of FIG. 8 in a counterclockwise direction through angle theta, and then ignoring the component represented by vector 110 while retaining only the component along the x' axis when making future measurements to check for structural cracks.

In order to accomplish this, values of sin theta and cos theta values are calculated using a right triangle shown in FIG. 8 in which voltage points $(x_1, y_1)$ and $(x_2, y_2)$ define the hypotenuse of the right triangle. In the present right triangle, $$\sin\theta = \text{opposite/hypotenuse} = -(x_2-x_1)/[(x_2-x_1)^2+(y_2-y_1)^2] \quad (1)$$

and $$\cos\theta = \text{adjacent/hypotenuse} = (y_2-y_1)/[(x_2-x_1)^2+(y_2-y_1)^2] \quad (2)$$

Figure 9:
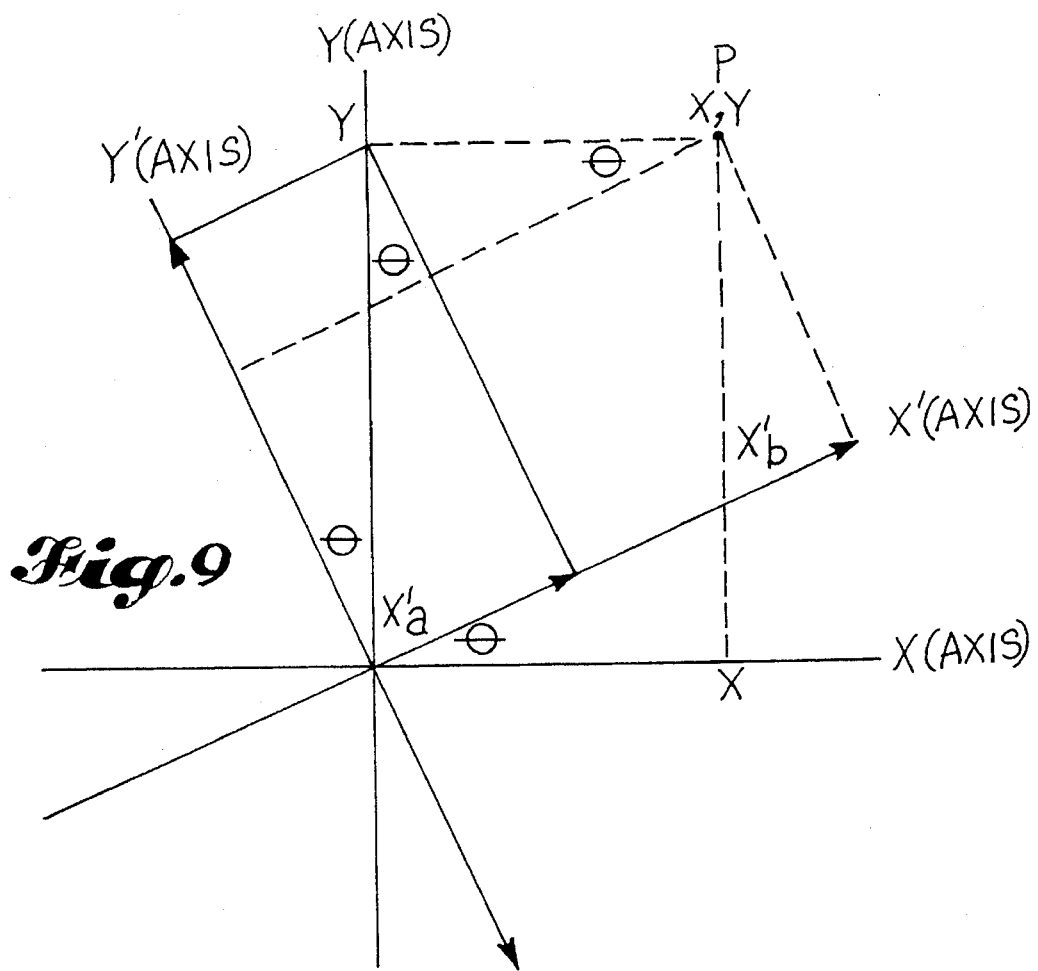
FIG. 9 is a graphical plot of x,y voltage components in a conventional coordinate system and a rotated coordinate system.

Since the real and imaginary components (x,y) of each voltage P is referenced to the original coordinate system, each of these components must be referenced to the rotated coordinate system. As shown in FIG. 9, the x' component of voltage is equal to the sum of vectors $x_a'+x_b'$. Furthermore, by simple trigonometry, $$x_a' = y \sin\theta, \text{ and} \quad (3)$$

$$x_b' = x \cos\theta \quad (4)$$

Therefore, $$x' = x \cos\theta + y \sin\theta. \quad (5)$$

Furthermore, since the purpose of the system is to measure a change in the voltage due to the presence of a crack, the initial liftoff voltage $x_1, y_1$ components are subtracted from the current voltage components x,y as follows:

$$x' = (x-x1) \cos\theta + (y-y1) \sin\theta, \quad (6)$$

and substituting for cos theta and sin theta, then $$x' = [ad/(c2+d^2)] - [bc/(c^2+d^2)] \quad (7)$$

where $a=x-x_1$; $b=y-y_1$; $c=x_2-x_1$; and $d=y_2-y_1$; and x' is the real component of the voltage value which is used to generate the monitor display.

Figure 10:
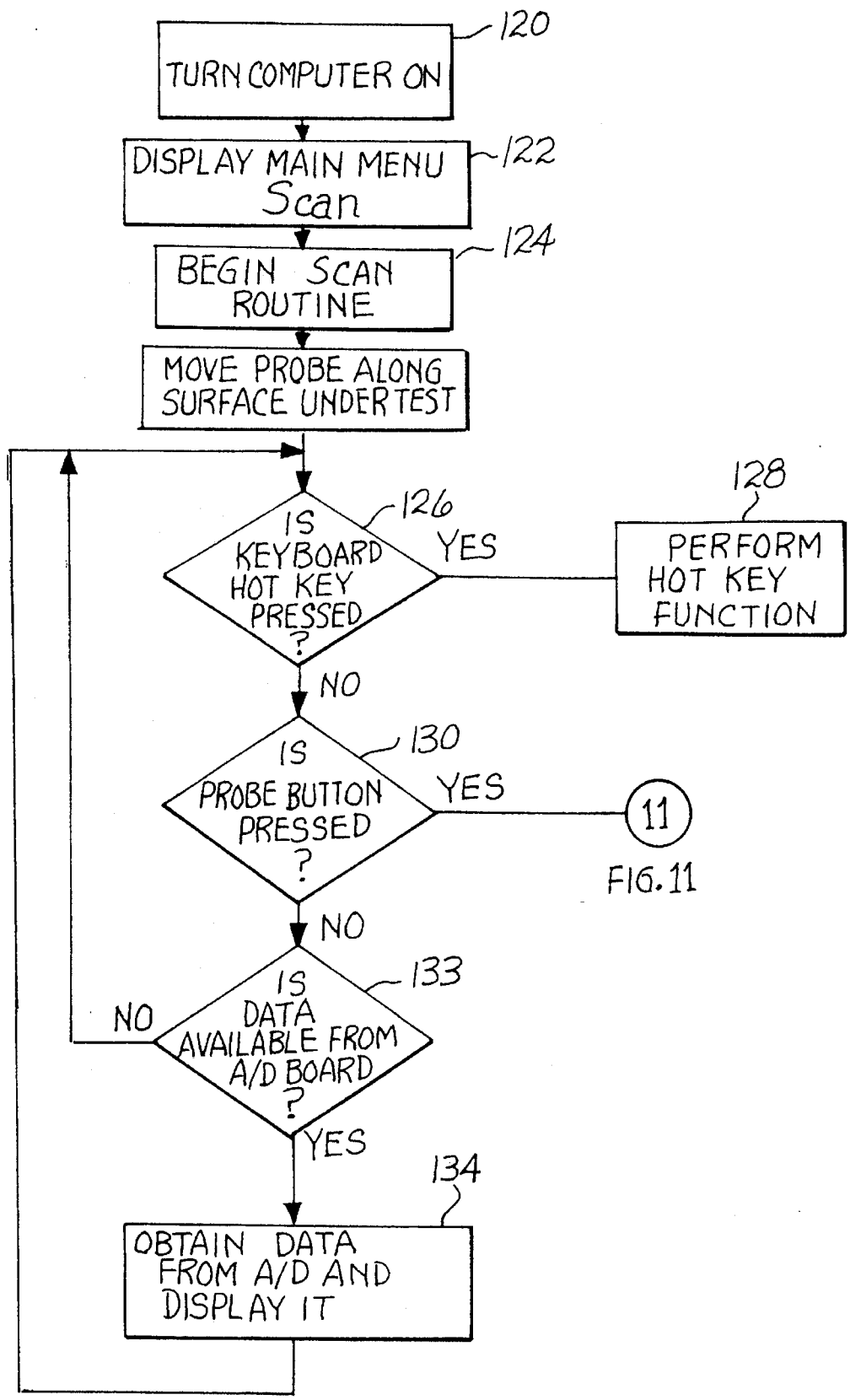
FIG. 10 is a flow chart describing an overview operation of the present invention.

Turning now to FIG. 10, an overview of the operating program stored in the memory of computer 34 will be described. When the computer 34 is turned on (block 120), a main menu is displayed on the monitor screen (block 122) which includes a scan routine. After selection of the scan routine (block 124), it is determined whether any of the individual "hot keys" have been pressed on the computer keyboard (block 126). More specifically, there are individual keys on the keyboard which are dedicated to initiating the performance of specific functions when pressed (block 128). Some of these functions include liftoff compensation, balance procedure, zero procedure, save files and print. Since these hot keys are not important to the present invention, they will not be discussed in further detail.

Figure 7:
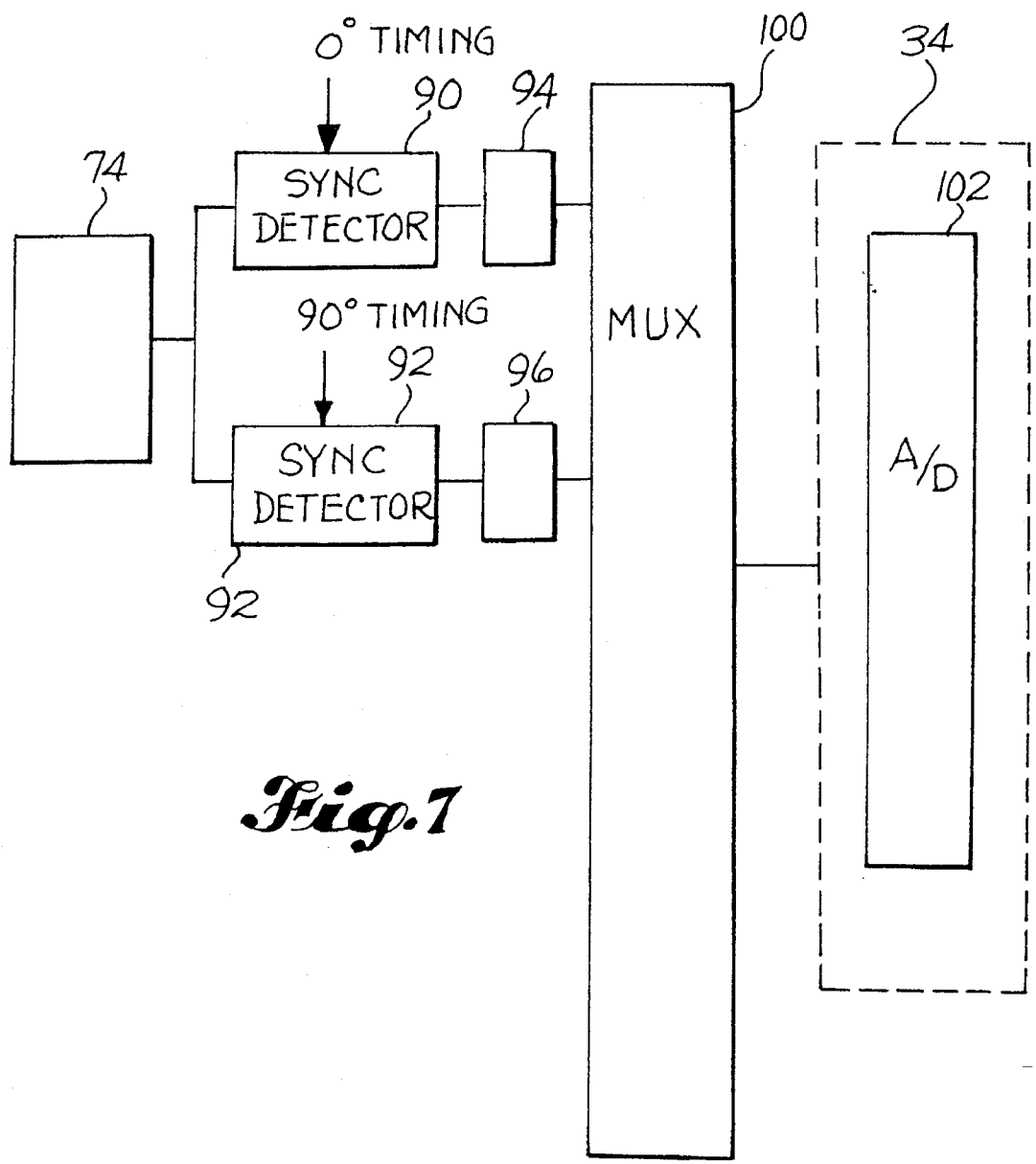

On the other hand, if none of the hot keys have been pressed, a question is raised whether the probe button 43 has been pressed (block 130). If the answer is yes, the "Compensation Procedure" menu is displayed (block 132 of FIG. 11 ) which includes options for selection of a "Liftoff Procedure", "Balance Procedure" or "Zero Procedure" (these procedures to be discussed later). Continuing with the overview, if the probe button 43 has not been pressed, a question is raised (block 133 of FIG. 10) whether any voltage data is available at the A/D board 102 (FIG. 7). If the answer is yes, the data is obtained from the A/D board and displayed at the monitor 36 (block 134) in a manner described in further detail in relation to FIG. 14.

Figure 11:
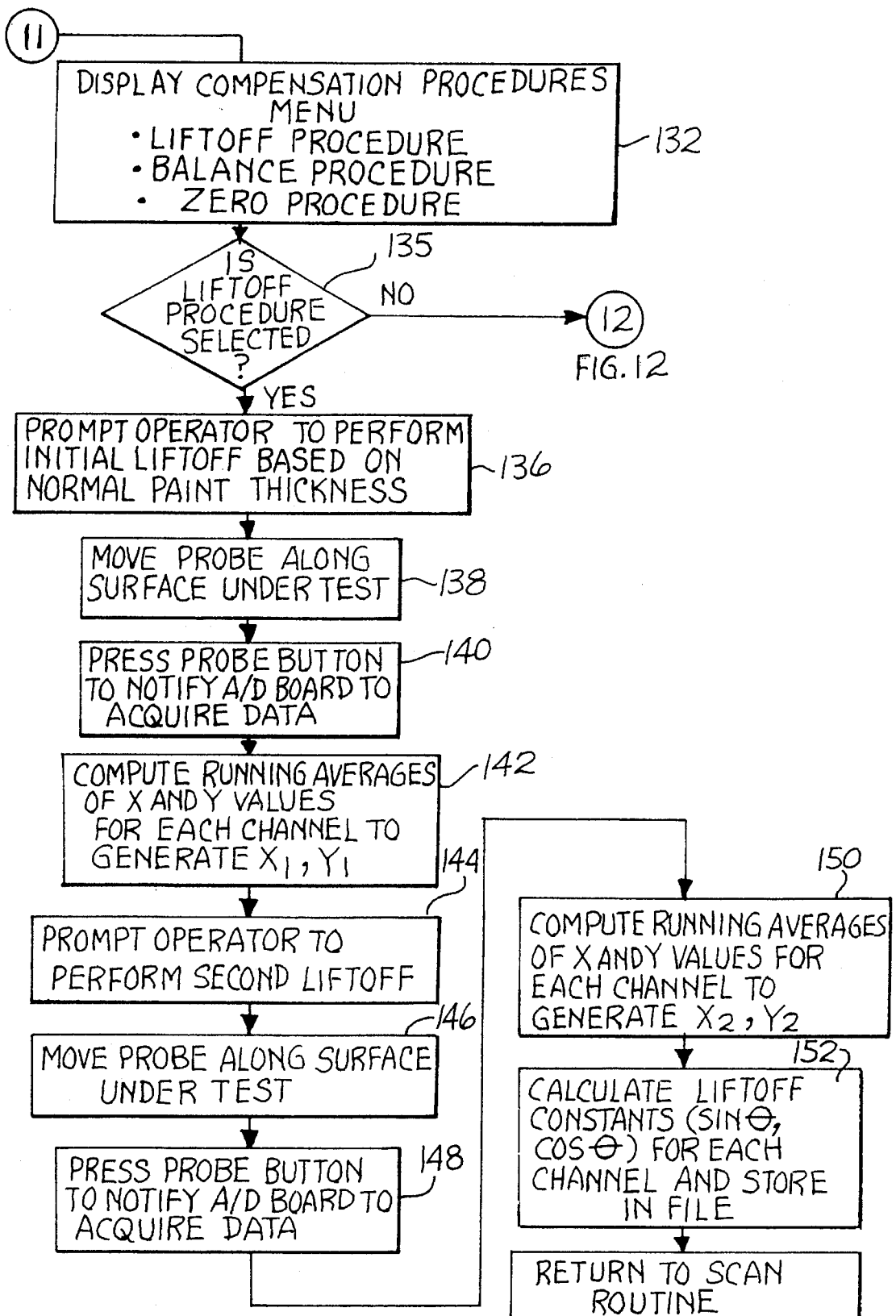
FIG. 11 is a flow chart describing calculation of liftoff constants.
Figure 14:
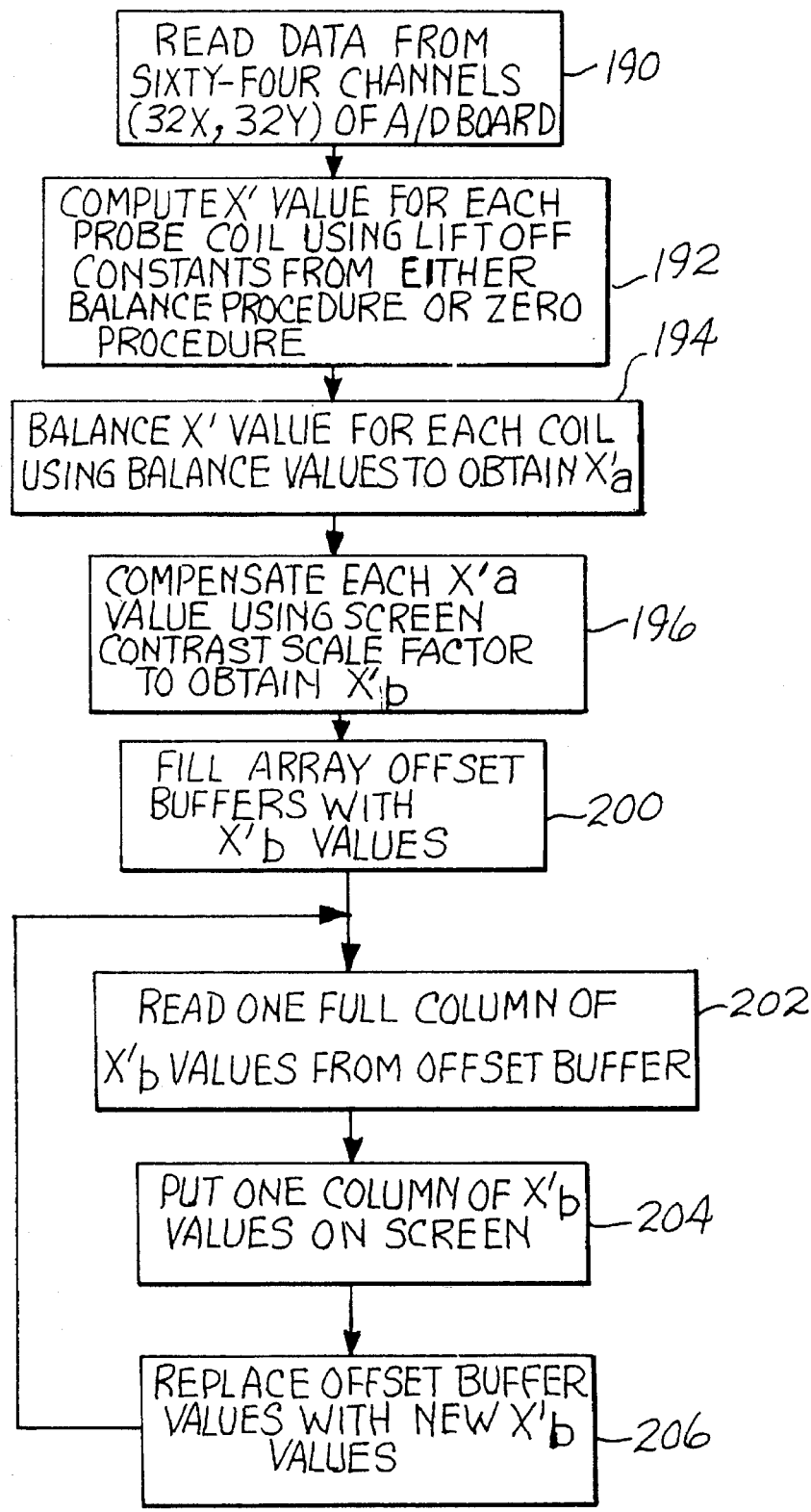
FIG. 14 is a flow chart describing data acquisition and display.

Before discussing the data acquisition and display procedures set forth in FIG. 14, attention will be turned to the liftoff, balance and zeroing procedures. As shown in FIG. 11, a question is raised whether the liftoff compensation procedure (block 135) has been selected. If the answer is yes, then the operator is prompted to perform initial liftoff (block 136) by moving the probe along the part-under-test a short distance (e.g., one inch). At the same time, the probe button 43 is pressed to notify the A/D board 102 to begin acquiring the voltage data (block 140). As discussed previously, the real and imaginary components (x,y) of each voltage measurement is determined, and these values are stored in the computer memory in a manner that a running average of the x values and running average of the y values are calculated and stored as $x_1$, $y_1$ in memory (block 142).

Upon completion of initial liftoff, the operator is prompted to perform a second liftoff (block 144) in which the probe is moved a short distance over several sheets of Mylar which are placed on top of the part under test (block 146) in the manner discussed previously. At the same time the probe button is pressed to notify the A/D board 102 to acquire the voltage data (block 148), and the running averages of the x and y voltage components for each channel are calculated to generate values $x_2$, $y_2$ (block 150). Using voltage component values $x_1$, $y_1$, $x_2$, $y_2$, the liftoff constants sin theta, cos theta are calculated (block 152) in accordance with equations (1) and (2). These voltage components are stored in a file for later use prior to returning to the scan routine (block 154) set forth in FIG. 10.

Figure 12:
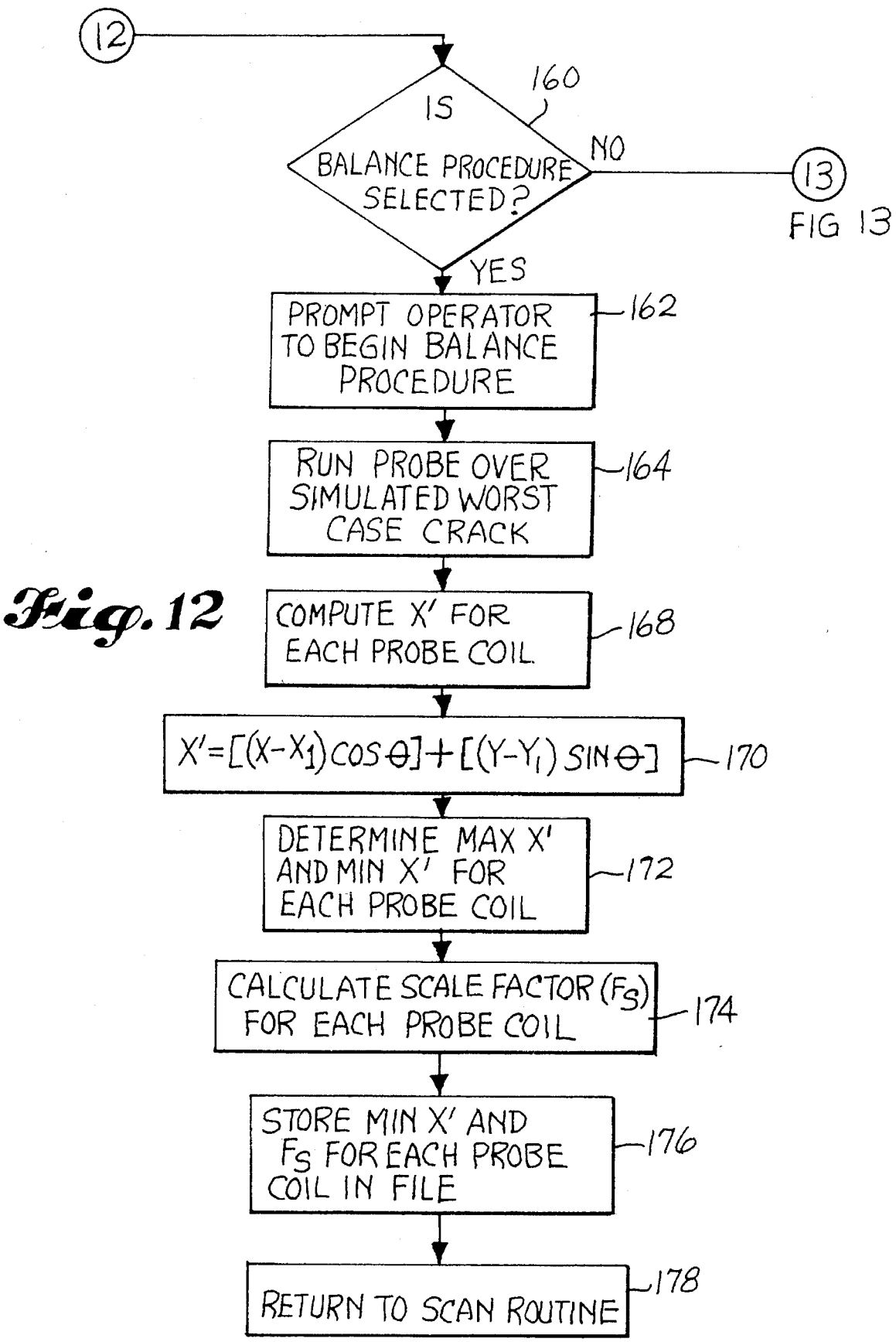
FIG. 12 is a flow chart describing calculation of balance factors.

On the other hand, if at decision block 135 (FIG. 11), the liftoff procedure is not selected, a question is raised whether the balance procedure has been selected by the operator (block 160 of FIG. 12). If the answer is "yes", the operator is prompted to begin the balance procedure (block 162). The purpose of the balance procedure is to generate compensation values for use in adjusting each of the thirty two channels so that their gains are evenly matched. This is accomplished by running the probe (block 164) over a simulated worst case crack (e.g. test panel having a crack as wide as the thirty two probe coils). The resulting voltage data is acquired from the A/D board 102, and an x' voltage value is computed for each coil using the equation set forth in block 170. Then the maximum x' (max x') and minimum x' (minx') values for each channel are calculated (block 172), and the maximum x' value (max $x'_{all}$) and minimum x' value (min $x'_{all}$) for all the channels is calculated. Using these values a scale factor ($F_S$) is calculated (block 174) for each channel wherein $$F_S = (\max x'_{all} - \min x'_{all})/(\max x'_{coil} - \min x'_{coil}) \tag{8}$$

The values minx' and $F_S$ for each channel are filed in memory (block 176) before returning to the scan routine (block 178) in FIG. 10.

Figure 13:
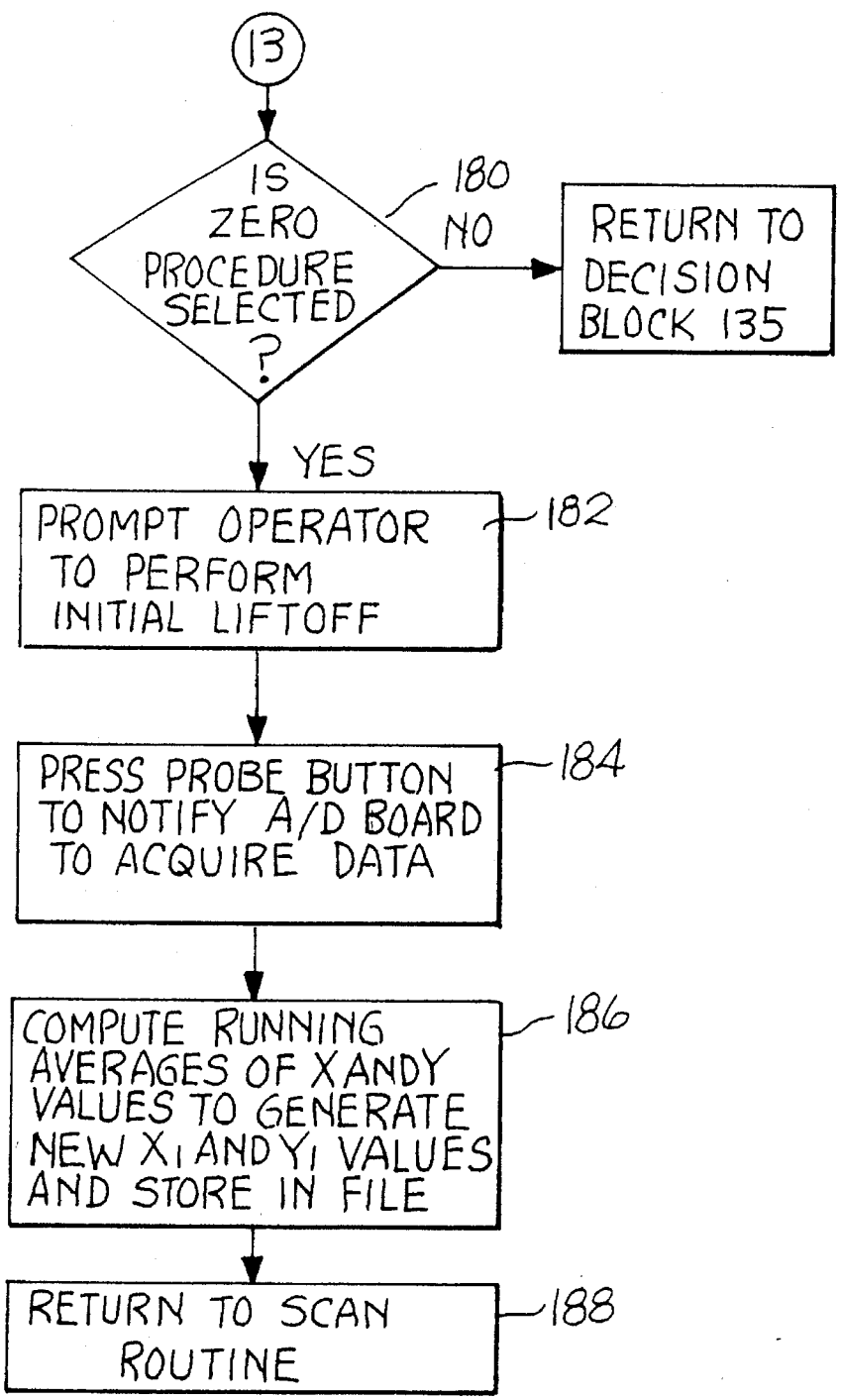
FIG. 13 is a flow chart describing a zeroing procedure.

In the event the decision at block 160 (FIG. 12) is "no", then it is determined whether the zero procedure has been selected (block 180 of FIG. 13). If the answer is "yes", the operator is prompted to perform initial liftoff (block 182) in the manner described previously with reference to block 136 of FIG. 11. Following this, the probe button is pressed to notify the A/D board 102 to acquire the voltage data (block 186). Running averages of the x and y component values are calculated and then stored in memory values as $x_1$, $y_1$, before returning to the scan routine. It should be appreciated that the purpose of the zeroing procedure is to provide a quick method of generating new values of $x_1$, $y_1$ which may vary due to any drifting of the electronic hardware because of heat or cold effects.

Returning now to the data acquisition and display procedure of block 134 of the scan routine (FIG. 10), this procedure is described in further detail in relation to FIG. 14. The procedure begins by moving the probe until an external trigger occurs (0.0125 inches) so as to acquire each of the thirty two x values and thirty two y values from the A/D board 102 (block 190). The x' value for each channel is calculated pursuant to equation (6) using the liftoff constants obtained from either the balance procedure and/or the zero procedure (block 192). Following this, the x' value for each coil is balanced to obtain an $x_a'$ value for each channel (block 194), wherein $$x_a' = (x' - \min x)(F_S) \tag{9}$$

In this manner, each channel value is compared to a standard value (min x) and multiplied by the scale factor ($F_S$).

Following this, each $x_a'$ value is further compensated using a screen contrast scale factor to obtain an $x_b'$ value (block 196). More specifically, to obtain the best display of the data on the monitor screen, it is desirable to maximize the contrast. The values of $x_a'$ occupy a gray scale from zero to ten. If, for example, there are sixteen colors available from the computer, then each of the $x_a'$ values is multiplied by a screen contrast scale factor of 16/10=1.6, for example, (to produce $x_b'$ values) to take full advantage of the color ranges available on the computer monitor.

Following this, the $x_b'$ values are stored in an offset compensation buffer (block 200). By way of background, it is apparent that as the probe proceeds over a structural crack, for example, the first data sample taken will be from those coils (1,9,18, and 25) in row #1 (identified by a number 201 in FIG. 3) of the probe. However, to obtain an accurate, high resolution display of the crack in the part-under-test, it is desirable that this initial data not be used to generate a visual display until the data from all thirty two coils has been collected. More specifically, since all of the probe coils do not pass a particular point on the part-under-test at the same time, it is necessary to store the initial data in the offset compensation buffer until data (representative of a particular location on the part-under-test) from all thirty two probe coils has been collected before displaying it.

Figure 15:
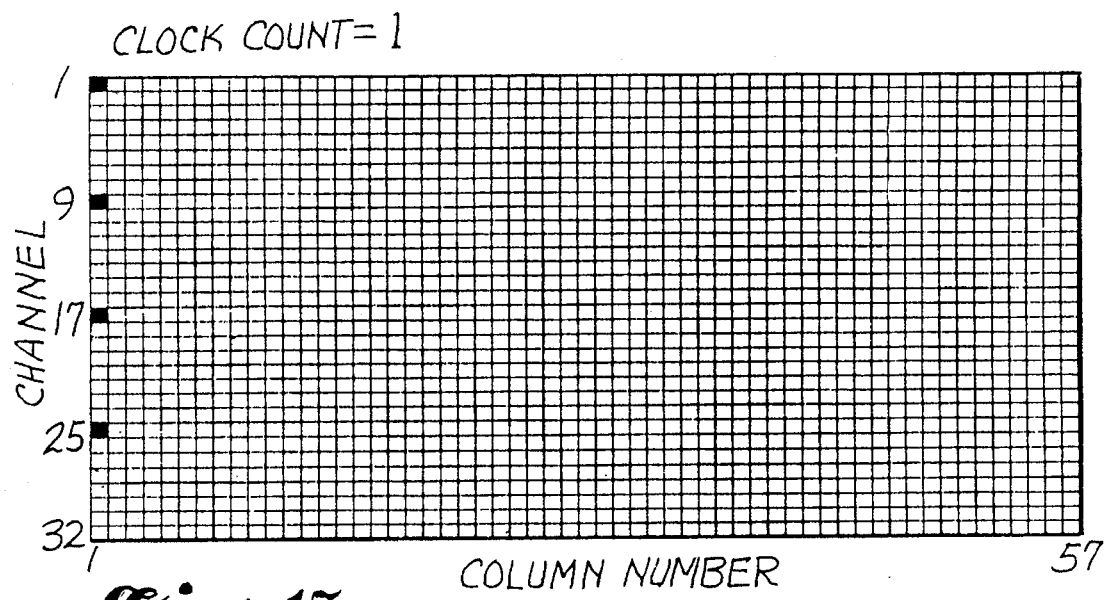
FIG. 15 is a graphical representation of data in an offset compensation buffer after one clock count.

Referring now to FIG. 15 there is shown a graphical representation of the offset compensation buffer for each of the thirty two channels (probe coils). In the present invention, the second row of the probe coils (identified by a 203 in FIG. 3) advances to the position previously occupied by the first row (201) of coils in eight clock counts; and the last row of coils (eighth row) reaches the position on the part-under-test initially occupied by the first row of coils after fifty six clock counts.

Figure 16:
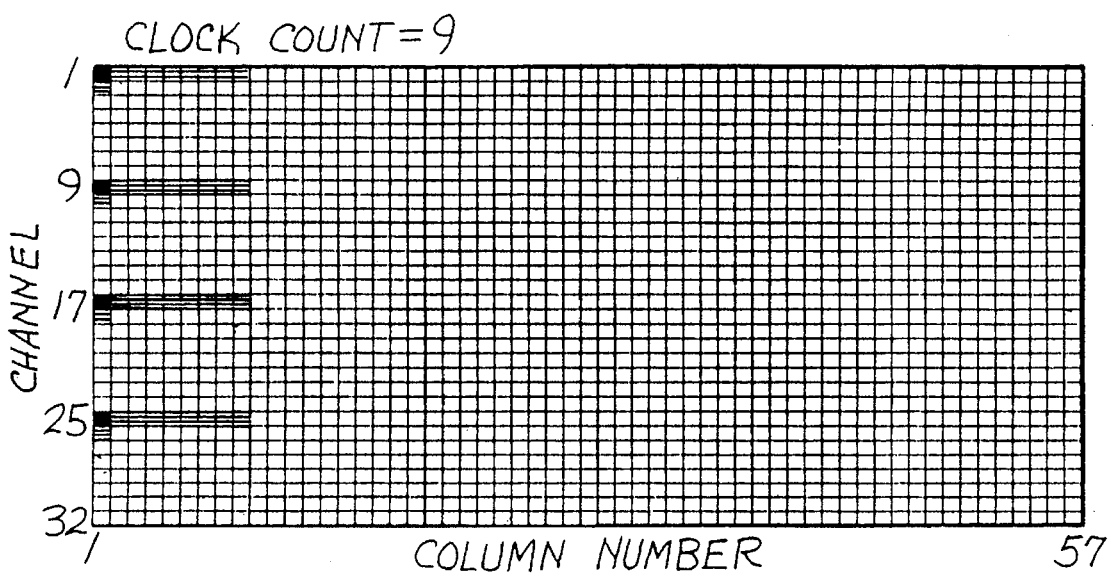
FIG. 16 shows the buffer of FIG. 15 after nine clock counts.
Figure 17:
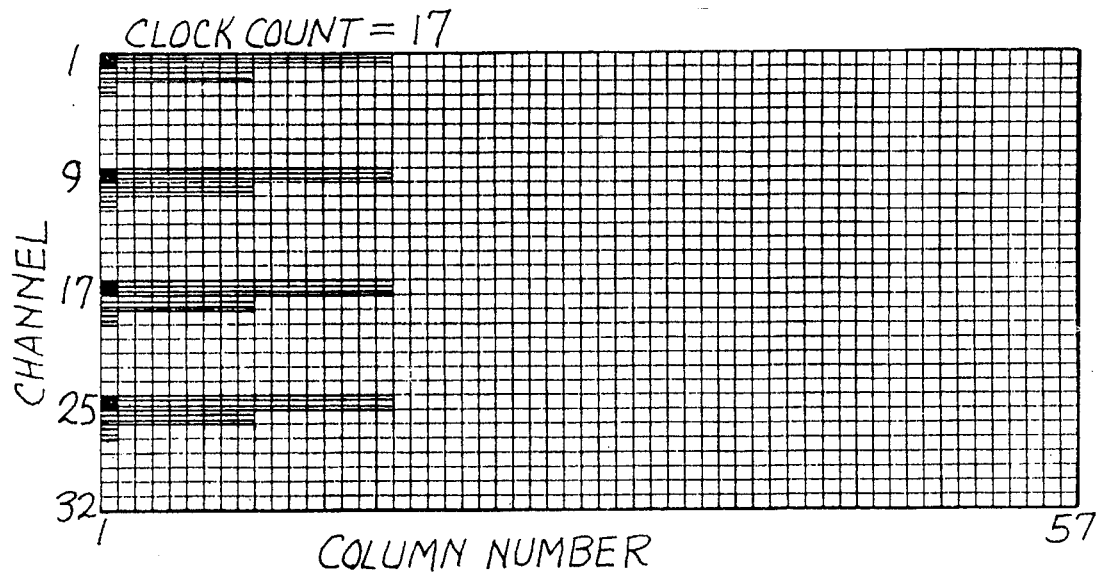
FIG. 17 shows the buffer of FIG. 15 after seventeen clock counts.

As shown in FIG. 15, after one clock count, data obtained from coils 1, 9, 17 and 25 is put into the buffer. Similarly, after eight clock counts, data is available only from channels 1, 9, 17 and 25 for placement in columns 2 through 8 of the buffer. However, on clock count #9, the second row (203 of FIG. 3) of probe coils moves into the position initially occupied by the first row (201) of the coils. Therefore data is available from the second row of coils (2, 10, 18, and 26) as shown in FIG. 16 for placement in the buffer. This data, however, is stored in column #1 of the buffer because the positions of coils 2, 10, 18 and 26 correspond to the positions initially occupied by coils 1, 9, 17 and 25 when the data from these coils was entered into column #1 eight clock counts previously. In addition, data is taken from coils 1, 9, 17 and 25 which is entered into column #9 since column #9 corresponds to the real time position of these coils with respect to the buffer. Similarly, after seventeen clock counts (FIG. 17), the third row of coils now occupies the very initial position of the first row of coils. Therefore the data from coils 3, 11, 19, and 27 is placed in column #1 of the buffer.

Figure 18:
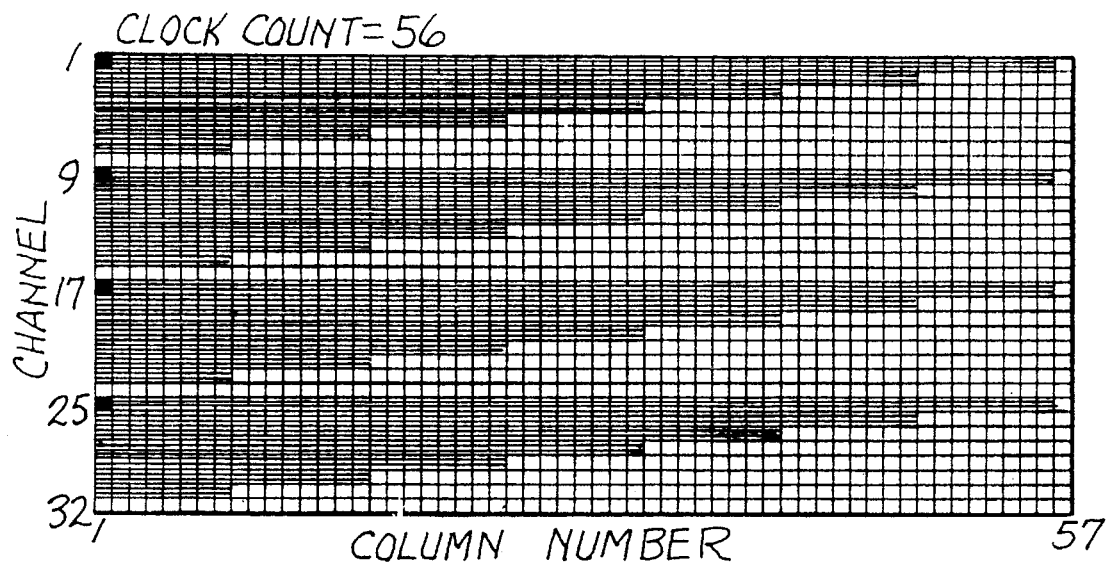
FIG. 18 shows the buffer of FIG. 15 after fifty six clock counts.
Figure 19:
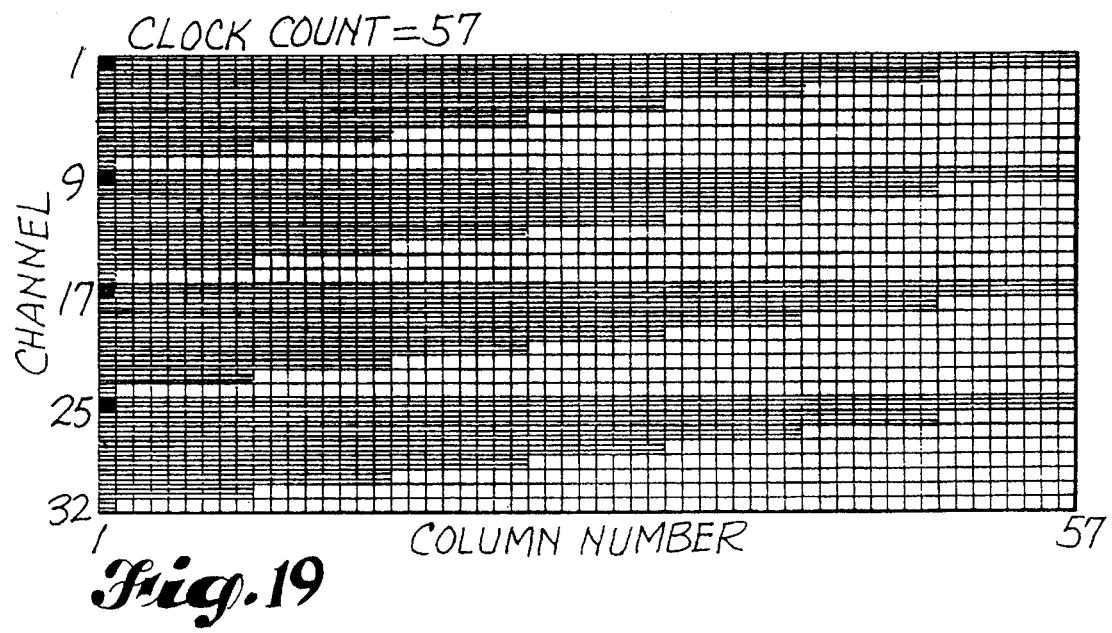
FIG. 19 shows the buffer of FIG. 15 after fifty seven clock counts.

In this manner, the offset compensation buffer is filled as shown in FIG. 18. However, after fifty seven clock counts, the last (eighth) row of probe coils occupies the position on the part-under-test initially occupied by the first row of coils. Therefore at clock count fifty seven, the data from coils 8, 16, 24 and 32 is entered into column #1 of the buffer as shown in FIG. 19. Thus, having filled column #1, the data from this column is then read for display on the monitor screen as a portion of the part-under-test.

Figure 20:
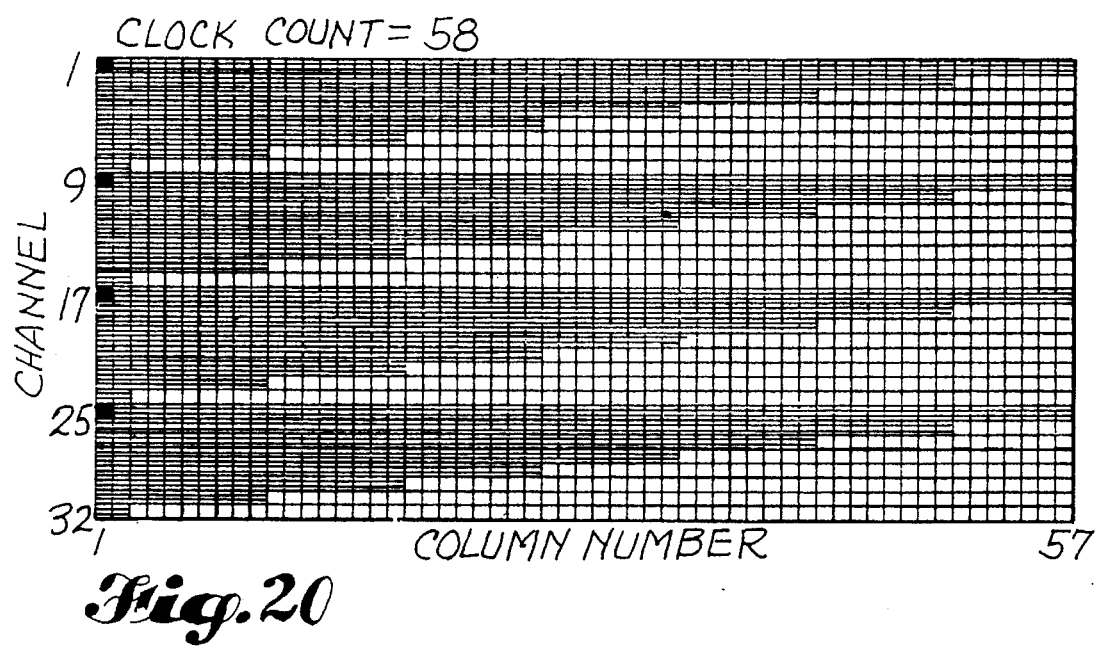
FIG. 20 shows the buffer of FIG. 15 after fifty eight clock counts.

Furthermore, at clock count fifty eight (FIG. 20), the buffer is "wrapped around" so that "new" data from coils 1, 9, 17 and 25 is used to renew a corresponding portion of the data in column #1, while at the same time this data completes the filling of column #2 so that the data from column #2 of the buffer can be read for display on the monitor screen. This procedure continues, with the data in column #1, for example, again being displayed only after all of the "old" data in that column has been replaced fifty seven clock counts after having being read for display on the monitor.

What is claimed is:

1. Apparatus for detecting a crack in a workpiece, the apparatus comprising:
   a. means, which are movable with respect to the workpiece, for detecting a change in an eddy current in the workpiece due to the presence of the crack when the detecting means is moved near the crack;
   b. means for generating a measurement signal which is a function of the change in the eddy current due to the presence of the crack such that the measurement signal has a first component when the detecting means moves in a first direction relative to the workpiece and a second component when the moving means moves in a second direction relative to the workpiece;
   c. means for removing the second component from the measurement signal, the second component removing means including
      (i) means for generating a first signal, represented by a vector having an endpoint x1,y1 of a vector coordinate system, resulting from movement of the detecting means relative to the workpiece,
      (ii) means for generating a second signal, represented by a vector having an endpoint x2,y2 of the vector coordinate system, resulting from movement of the detecting means relative to the workpiece, such that the second signal differs from the first signal due to movement of the detecting means in the second direction relative to the workpiece,
      (iii) means for calculating a compensation vector extending between endpoint x1,y1 and endpoint x2,y2,
      (iv) means for rotating the vector coordinate system so that an axis of the vector coordinate system is parallel to the compensation vector,
      (iv) means for referencing the first component and the second component of the measurement signal to the rotated vector coordinate system, and
      (v) means for removing the second component of the measurement signal by ignoring any components of the measurement signal in the rotated vector coordinate system which are parallel to the compensation vector; and
   d. means for generating a visual display of the crack as a function of the first component of the measurement signal.

2. The apparatus as set forth in claim 1 wherein the second signal generating means includes means for generating the second signal during movement of the detecting means along a location of the workpiece which is the same as the location during generation of the first signal, and at a vertical distance from the workpiece which is different from the vertical distance from the workpiece during generation of the first signal.

3. The apparatus as set forth in claim 2 wherein the measurement signal generating means includes means for generating the second component of the measurement signal when movement of the detecting means moves in the second direction is a vertical direction relative to the workpiece.

4. Method for detecting a crack in a workpiece, the method comprising the following steps:
   a. detecting a change in an eddy current in the workpiece due to the presence of the crack when a detector is moved near the crack;
   b. generating a measurement signal which is a function of the change in the eddy current due to the presence of the crack such that the measurement signal has a first component when the detector moves in a first direction relative to the workpiece and a second component when the detector moves in a second direction relative to the workpiece;
   c. removing the second component from the measurement signal by
      (i) generating a first signal, represented by a vector having an endpoint x1,y1 of a vector coordinate system, resulting from movement of the detector relative to the workpiece,
      (ii) generating a second signal, represented by a vector having an endpoint x2,y2 of the vector coordinate system, resulting from movement of the detector relative to the workpiece, such that the second signal differs from the first signal due to movement of the detector in the second direction relative to the workpiece,
      (iii) calculating a compensation vector extending between endpoint x1,y1 and endpoint x2,y2,
      (iv) rotating the vector coordinate system so that an axis of the vector coordinate system is parallel to the compensation vector,
      (iv) referencing the measurement signal to the rotated vector coordinate system, and
      (v) removing the second component of the measurement signal by ignoring any components of the measurement signal in the rotated vector coordinate system which are parallel to the compensation vector; and
   d. generating a visual display of the crack as a function of the first component of the measurement signal.

5. The method as set forth in claim 4 wherein the second signal generating step includes generating the second signal during movement of the detecting means along the same location of the workpiece as during generation of the first signal and at vertical distance from the workpiece which is different from the vertical distance from the workpiece during generation of the first signal.

6. Apparatus for detecting a crack in a workpiece, the apparatus comprising:
   a. means, which are movable with respect to the workpiece, for detecting a change in an eddy current in the workpiece due to the presence of the crack when the detecting means is moved near the crack during an x clock count and a y clock count, the detecting means including a first row of detector elements for detecting the presence of the crack and for generating first signals at the x clock count and first signals at the y clock count, and a second row of detector elements for detecting the presence of the crack and for generating second signals at the clock count, the first and second row of detector elements being located in the detecting means such that the first row of detecting elements are moved near the crack before the second row of detecting elements are moved near the crack;

b. means for generating a signal which is a function of the change in the eddy current due to the presence of the crack, the signal generating means including means for storing the first and second signals, the storing means including a first location for storing the first signals obtained at the x clock count and for storing the second signals obtained at the y clock count, and a second location for storing the first signals obtained at the y clock count such that the signals stored in the first location are representative of a first portion of the crack and the signals stored in the second location are representative of a second portion of the crack; and c. means for generating a visual display of the workpiece such that the signals from the first and second columns generate a visual display of the first and second portions of the crack.

7. The apparatus as set forth in claim 6 wherein:

a. the detecting means is moved near the crack during the x clock count, the y clock count and a z clock count;

b. the detecting means is movable with respect to the workpiece such that the first row of detector elements generates third signals at the z clock count which are representative of a third portion of the crack;

c. the signal generating means includes means for replacing the first signals with the third signals in the first location at the third clock count; and d. the visual display generating means includes means for generating a visual display of the workpiece such that the signals from the first column generates a visual display of the third portion of the crack.

* * * * *